United States Patent
Hintzer et al.

(10) Patent No.: US 9,694,333 B2
(45) Date of Patent: Jul. 4, 2017

(54) RECOVERY OF BRANCHED FLUORINATED EMULSIFIERS

(71) Applicant: 3M INNOVATIVE PROPERTIES COMPANY, St. Paul, MN (US)

(72) Inventors: Klaus Hintzer, Kastl (DE); Egon Obermaier, Taubenbach (DE); Arne Thaler, Emmerting (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 15/302,525

(22) PCT Filed: Apr. 15, 2015

(86) PCT No.: PCT/US2015/025937
§ 371 (c)(1),
(2) Date: Oct. 7, 2016

(87) PCT Pub. No.: WO2015/160926
PCT Pub. Date: Oct. 22, 2015

(65) Prior Publication Data
US 2017/0028370 A1    Feb. 2, 2017

Related U.S. Application Data

(60) Provisional application No. 61/981,237, filed on Apr. 18, 2014.

(51) Int. Cl.
| | |
|---|---|
| *C07C 51/42* | (2006.01) |
| *B01F 17/00* | (2006.01) |
| *B01J 49/07* | (2017.01) |
| *B01J 49/57* | (2017.01) |
| *B01J 41/12* | (2017.01) |
| *B01J 41/05* | (2017.01) |

(52) U.S. Cl.
CPC ........... *B01F 17/0035* (2013.01); *B01J 41/05* (2017.01); *B01J 41/12* (2013.01); *B01J 49/07* (2017.01); *B01J 49/57* (2017.01)

(58) Field of Classification Search
CPC .................................................. B01F 17/0035
USPC .......................................................... 562/580
See application file for complete search history.

(56) References Cited

U.S. PATENT DOCUMENTS

| | | |
|---|---|---|
| 5,312,935 A | 5/1994 | Mayer |
| 5,763,552 A | 6/1998 | Feiring |
| 6,436,244 B1 | 8/2002 | Fuhrer |
| 7,754,914 B2 | 7/2010 | Fuhrer |
| 7,807,726 B2 | 10/2010 | Maurer |
| 2006/0205828 A1 | 9/2006 | Maurer |
| 2007/0015865 A1 | 1/2007 | Hintzer |
| 2007/0015937 A1 | 1/2007 | Hintzer |
| 2007/0025902 A1* | 2/2007 | Hintzer .................. C08L 27/12 423/240 S |
| 2008/0182913 A1 | 7/2008 | Higuchi et al. |
| 2009/0281261 A1 | 11/2009 | Brothers |

FOREIGN PATENT DOCUMENTS

| | | |
|---|---|---|
| EP | 1856165 | 11/2007 |
| WO | WO 2005-077880 | 8/2005 |
| WO | WO 2009-137734 | 11/2009 |

OTHER PUBLICATIONS

"Encyclopedia of Polymer Science and Engineering", Identification to Lignin, John Wiley & Sons, 1985, vol. 8, pp. 347-353.
Kirk-Othmer, "Encyclopedia of Chemical Technology", Hydrogen-ion Activity to laminated materials, glass, John Wiley & Sons, 3$^{rd}$ edition, vol. 13, pp. 687-688.
International Search report for PCT International Application No. PCT/US2015/025937 mailed on Jul. 16, 2015, 7 pages.

* cited by examiner

*Primary Examiner* — Deborah D Carr
(74) *Attorney, Agent, or Firm* — Julie Lapos-Kuchar

(57) ABSTRACT

Described herein is a process for recovering a branched, ether-containing fluorinated emulsifier from an anion exchange resin by (1) contacting the anion exchange resin with a recovery fluid to form an eluate, the recovery fluid comprising an ammonium salt, water, and a water-miscible solvent, wherein the fluorinated emulsifier is of the formula: [Rf-(0-R'f)n-0-CF(CF3)-C(0)0-]i M+1; and (2) separating the anion exchange resin from the eluate.

13 Claims, No Drawings

RECOVERY OF BRANCHED FLUORINATED EMULSIFIERS

CROSS REFERENCE TO RELATED APPLICATIONS

This application is a national stage filing under 35 U.S.C. 371 of PCT/US2015/025937, filed Apr. 15, 2015, which claims the benefit of U.S. Application No. 61/981,237, filed Apr. 18, 2014, the disclosure of which is incorporated by reference in its/their entirety herein.

TECHNICAL FIELD

The present invention relates to recovery of an anionic branched fluorinated emulsifier from an anion exchange resin.

SUMMARY

In accordance with one aspect, a process is provided comprising recovering a fluorinated emulsifier from an anion exchange resin, by contacting the anion exchange resin with a recovery fluid to form an eluate, the recovery fluid comprising an ammonium salt, water, and a water-miscible solvent, wherein the fluorinated emulsifier is of the formula:

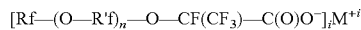

$$[Rf-(O-R'f)_n-O-CF(CF_3)-C(O)O^-]_i M^{+i}$$

wherein Rf is a fluorinated alkyl group comprising 1 to 5 carbon atoms; R'f is a divalent fluorinated group comprising 1 to 5 carbon atoms; n is 0, 1, 2, or 3; and $M^{+i}$ represents a cation having the valance i and i is 1, 2 or 3; and separating the anion exchange resin from the eluate.

The process according to the invention may provide one or more of the following advantages. For example, the process can be designed to allow for recovery of the branched fluorinated emulsifier from an anion exchange resin. The branched fluorinated emulsifier can be regenerated back to its original form for reuse in a subsequent polymerization process. Also, the recovery fluid used for recovering the fluorinated emulsifier from the anion exchange resin can be readily and cost effectively manufactured. Further the process may be carried out in a convenient and easy manner. Furthermore, the method generally does not require large amounts of the recovery fluid and it avoids the formation of highly volatile fluorinated compounds (e.g., esters).

The above summary is not intended to describe each embodiment. The details of one or more embodiments of the invention are also set forth in the description below. Other features, objects, and advantages will be apparent from the description and from the claims.

DETAILED DESCRIPTION

As used herein, the term

"a", "an", and "the" are used interchangeably and mean one or more; and

"and/or" is used to indicate one or both stated cases may occur, for example A and/or B includes, (A and B) and (A or B).

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

In 2006, the US Environmental Protection Agency initiated a PFOA Stewardship Program aimed at reducing facility emissions and product content of PFOA (perfluorooctanoic acid) and related chemicals on a global basis by 95% by 2010 and eliminating the emissions and product content of PFOA and related chemicals by 2015. At the time, PFOA was the standard emulsifier used in the aqueous polymerization of fluoropolymers.

Because of its expense and to avoid undesirable release in the environment, PFOA was removed from the dispersions and waste streams (waste water and exhaust gas) generated in the manufacturing of the fluoropolymer.

U.S. Pat. No. 7,754,914 (Fuhrer, et al.) discloses the recovery of (per)fluorinated aliphatic acid emulsifiers, or salts thereof, from adsorbent particles such as ion exchange resins. In this patent, the adsorbent particles comprising the fluorinated emulsifier are mixed with a recovery fluid, comprising alcohol and optionally an acid and water. The mixture is heated to cause esterification of the (per)fluorinated aliphatic acid emulsifier. The mixture then is distilled to separate and collect the esterified fluorinated emulsifier, which is then converted back to the corresponding fluorinated acid emulsifier (or salt thereof) by hydrolyzing the ester derivative. This process forms the highly volatile APFO-ester, but was found to be highly effective for recovery of PFOA.

PFOA is being replaced in fluoropolymer polymerizations by more environmentally-friendly fluorinated emulsifiers, such as ether-containing fluorinated carboxylic acids or salts thereof. The esterification and distillation of these new emulsifiers are described in U.S. Pat. Publ. No. 2007/0025902 (Hintzer et al.), which showed a recovery efficiency of about 88% for $CF_3O(CF_2)_3O-CHF-CF_2COONH_4$ from an anion exchange resin. The recovered emulsifier was regenerated from the ester derivative back to the acid form and can be used in a subsequent polymerization. See Comparative Examples 1 and 2 below.

The esterification process of the fluorinated emulsifier described above allows for the removal of the fluorinated emulsifier from the ion exchange resin, while simultaneously purifying the fluorinated emulsifier for reuse. Further, this recovery, regeneration, and purification can be performed with minimal process steps in an efficient manner.

However, when this esterification technique (in other words, heating a free acid fluorinated emulsifier in the presence of alcohol to form the ester) followed by distillation is applied to a fluorinated emulsifier comprising an ether linkage and a branched group, the recovery of the fluorinated emulsifier is inadequate. For example, it can take a long time to separate the methyl ester derivative via distillation. Also, the conversion of the methyl ester derivative of the fluorinated emulsifier into a usable $NH_4$-salt (for re-use) is difficult because when the methyl ester derivative of a branched fluorinated emulsifier is treated with ammonia, the result is the formation of amides. See Comparative Examples 3-5 below.

It has been discovered that a method utilizing a recovery fluid comprising an ammonium salt, water, and a water-miscible solvent can be used to provide sufficient recovery of the fluorinated emulsifier comprising branching and at least one ether linkage, while not forming the amide derivative. See Example 1 below. Optionally, the recovered fluorinated emulsifier can then be regenerated back to its original form for reuse. Described below are further details of the present invention.

An aqueous composition comprising the fluorinated emulsifier is contacted with an anion exchange resin, which retains the fluorinated emulsifier. Such an aqueous composition can be, for example, a waste stream of the fluoropolymer production or a fluoropolymer dispersion containing the fluorinated emulsifier. The present disclosure is directed towards the recovery of this fluorinated emulsifier, specifically a branched fluorinated emulsifier comprising at least one ether linkage, from the anion exchange resin. A regenerating liquid comprising an ammonium salt, water, and a water-miscible solvent is used to recover the branched fluorinated emulsifier from the anion exchange resin.

Branched Fluorinated Emulsifier

The present disclosure is directed toward fluorinated emulsifiers comprising at least one ether linkage (hereinafter referred to as "branched fluorinated emulsifiers") of the formula

$[Rf—(O—R'f)_n—O—CF(CF_3)—C(O)O^-]_iM^{+i}$ wherein Rf is a fluorinated alkyl group comprising 1 to 5 carbon atoms; R'f is a divalent fluorinated group comprising 1 to 5 carbon atoms; n is 0, 1, 2, or 3; and $M^{+i}$ represents a cation having the valance i and i is 1, 2 or 3.

Rf is a monovalent fluorinated alkyl group comprising 1, 2, 3, 4, or 5 carbon atoms. Rf may be partially fluorinated or fully fluorinated, optionally comprising 1 or more halogens (e.g., Cl or Br). Exemplary Rf groups include: —$CF_3$, —$CF_2CF_3$, —$CF_2CF_2CF_3$, —$CF_2CF_2CHF_2$, —$CF_2CF_2CF_2Cl$, and —$CF_2CF_2CF_2Br$.

R'f is a divalent fluorinated group comprising 1, 2, 3, 4, or 5 carbon atoms. R'f may be linear or branched. R'f may be partially fluorinated or fully fluorinated, optionally comprising 1 or more halogens (e.g., Cl or Br). Exemplary R'f groups include: —$CF_2$—, —$CF_2CF_2$—, —$CF_2CF(CF_3)$—, and —$CF_2$—$CF_2$—$CF_2$—, —$CF_2$—$CHF$—$CF_2$—, —$CF_2$—$CF_2$—$CF_2$—$CF_2$—, and $CF_2$—$CF(CF_3)$—$CF_2$—.

$M^{+i}$ represents a cation having the valance i. M represents H, an alkali metal (e.g., Na, Ca, etc.), ammonium ($NH_4$), and $NR_4$ wherein each R is independently selected from H, and a C1-C5 alkyl group.

The branched fluorinated emulsifiers of the present disclosure comprise at least one ether linkage (e.g., at least 2, at least 3 or even at least 4 ether linkages) and at least one branched group (e.g., at least 2, at least 3 or even at least 4 branched groups). In one embodiment, the branched fluorinated emulsifier is fully fluorinated comprising no carbon-hydrogen bonds.

Generally, the branched fluorinated emulsifiers of the present disclosure will be a low molecular weight compound, for example a compound having a molecular weight for the anionic part of the compound of not more than 800 g/mol, 700 g/mol, 600 g/mol, or even 500 g/mol.

Exemplary branched fluorinated emulsifiers of the present disclosure include: $CF_3$—$CF_2$—$CF_2$—O—$CF(CF_3)$—C(O)—OH, $C_3F_7$—(O—$CF_2$—$CF(CF_3)$)$_2$—O—$CF(CF_3)$—C(O)OH, $C_3F_7$—(O—$CF_2$—$CF(CF_3)$)$_2$—O—$CF(CF_3)$—C(O)OH, $C_3F_7$—(O—$CF_2$—$CF(CF_3)$)$_3$—O—$CF(CF_3)$—C(O)OH, $CF_3$—(O—$CF(CF_3)CF_2$)—O—$CF(CF_3)$—C(O)OH, $CF_3$—O—$(CF_2)_2$—O—$CF(CF_3)$—C(O)OH, $CF_3$—O—$(CF_2)_3$—O—$CF(CF_3)$—C(O)OH, and their corresponding salts.

Anion Exchange Resin

The method of the present invention may be used to recover a variety of branched fluorinated emulsifiers from an anion exchange resin.

Examples of anion exchange resin that can be used to adsorb a fluorinated emulsifier include strong, medium strong as well as weak basic anion exchange resins. The terms strong, medium strong and weak basic anion exchange resin are defined in "Encyclopedia of Polymer Science and Engineering", John Wiley & Sons, 1985, Volume 8, page 347 and "Kirk-Othmer", John Wiley & Sons, 3$^{rd}$ edition, Volume 13, page 687. Strong basic anion exchange resin typically contain quaternary ammonium groups, medium strong resins usually have tertiary amine groups and weak basic resins usually have secondary amines as the anion exchange functions. Examples of anion exchange resins that are commercially available include those available under the trade designations "AMBERLITE IRA-402", "AMBERJET 4200", "AMBERLITE IRA-67" and "AMBERLITE IRA-92" all available from Dow Chemical Co., Midland, Mich.; "PUROLITE A845" available from Purolite GmbH, Ratingen, Germany; and "LEWATIT MP-500" available from Bayer AG, Leverkusen, Germany.

The anion exchange resin, may comprise a particle size distribution which is unimodial or multimodal (e.g., bimodal or trimodal).

Recovery Fluid

In the present disclosure, a recovery fluid comprising an ammonium salt, water, and a water-miscible solvent is used to recover the branched fluorinated emulsifier from the anion exchange resin.

The ammonium salts for use in connection with the present disclosure include organic as well as inorganic salts. Generally, the ammonium salt will be an inorganic ammonium salt. In an alternative embodiment, the ammonium salt may be an organic ammonium salt, in particular, one in which the anion of the salt is organic, such as for example a carboxylic anion.

According to a particular embodiment of the invention, the ammonium salt is one that corresponds to the general formula:

$(NR_4)_nX$ wherein R is independently selected from H or an alkyl group comprising 1-5 carbon atoms; n is 1, 2 or 3; and X is selected from F, Cl, Br, I, or an anionic organic residue. Particular examples of inorganic anions include halogen or halogen containing inorganic anions such as for example $F^-$, $Cl^-$, $Br^-$, $I^-$, $ClO_4^-$, phosphates, sulfates, sulphonates, and carbonates including $HCO_3^-$, and $CO_3^{2-}$, and $^-OOC$—$COO^-$. Examples of anionic organic residues include in particular carboxylic anions such as for example $HCOO^-$, and $CH_3COO^-$.

The appropriate amount of ammonium salt in the recovery fluid used for recovering the branched fluorinated emulsifier can be readily determined by one skilled in the art through routine experimentation. The amount will generally depend on the nature of the anion exchange resin and the amount of branched fluorinated emulsifier adsorbed on the anion exchange resin and/or the percentage of recovery that is desired. A suitable amount of ammonium salt is generally at least 0.1% by weight. According to a particular embodiment, the amount of ammonium salt is between 0.2 and 5% by weight based on the total weight of the recovery fluid used for eluting the exchange resin. In another embodiment, in amount of ammonium salt between 1 and 3% by weight may be used. The amounts of ammonium salt recited merely serve as guidance and are not intended to exclude the use of amounts of ammonium salt outside the range stated. For example, amounts of ammonium salt of less than 0.1% by weight or more than 5% by weight may be suitable in particular circumstances.

The recovery fluid comprises water. In one embodiment, water may for example be used in an amount of up to 45% by weight, for example in an amount of 0.1 to 40% by weight or in amount between 1 and 15% by weight or in an amount between 4 and 10% by weight.

The recovery fluid also includes a water-miscible solvent. By 'water miscible solvent' is generally meant an organic solvent that has solubility in water of at least 5% by weight, for example at least 10% by weight or at least 20% by weight. Suitable water-miscible solvents are typically polar solvents including for example alcohols, ketones, ethers and mixtures thereof. Particular examples of solvents include lower aliphatic alcohols having between 1 and 5 carbon atoms such as for example methanol, ethanol, and propanol; glycols, mono- and dialkyl ethers or monoglycol and diglycol wherein the alkyl groups have between 1 and 4 carbon atoms; and ketones such as acetone and methyl ethyl ketone.

The amount of water-miscible solvent may vary widely, but should generally be enough to dissolve the ammonium salt. According to an embodiment, the amount of water-miscible organic solvent is at least 50% by weight of the total weight of the recovery fluid. Exemplary ranges are 50 to 99% by weight, or between 60 and 90% by weight or between 90 and 98% by weight.

The recovery fluid may contain further components that may aid in the recovery of the branched fluorinated emulsifier from the anion exchange resin. For example, a base may be used to adjust the pH of the recovery fluid. In one embodiment, the pH of the recovery fluid used to recover the branched fluorinated emulsifier from the anion exchange resin is at a pH of greater then 5, 6, 7, or even 8, preferably greater than 6 or 7. When the pH of the recovery fluid is greater than 6, it is believed that no esterification of the branched fluorinated emulsifier will occur. Suitable bases that may be used are alkali metal hydroxides such as for example sodium hydroxide and potassium hydroxide. Other bases that may be used include earth alkali metal hydroxides, aluminum hydroxide or alcolates such as for example sodium methylate. When present, the amount of base included in the recovery fluid is generally up to about 5% by weight. An exemplary range is from 0.1 to 5% or from 0.5 to 2% by weight based on the total weight.

In one embodiment, the recovery fluid is substantially free of a strong acid (e.g., sulfuric acid, nitric acid, etc.).

Process

The anion exchange resin loaded with branched fluorinated emulsifier may be eluted with the recovery fluid described above by contacting the recovery fluid with the load anion exchange resin. Typically, the recovery of the emulsifier is carried out by pumping the recovery fluid over the loaded anion exchange resin held in a column. Upon exiting the column, the eluate will contain the branched fluorinated emulsifier or a derivative thereof. The branched fluorinated emulsifier or derivative thereof, may then be recovered from this eluate by suitable separation methods such as distillation, extraction or evaporation of the liquid phase (e.g., water/organic solvent). Alternatively, the anion exchange resin may be treated with the recovery fluid by gently stirring the loaded anion exchange resin with the recovery fluid followed by separating the anion exchange resin from the eluate (i.e., the recovery fluid comprising the branched fluorinated emulsifier or derivative thereof), for example, by filtration.

The amount of recovery fluid that is needed to recover the branched fluorinated emulsifier from the anion exchange resin depends on the amount and nature of the branched fluorinated emulsifier that is adsorbed on the anion exchange resin as well as on the composition of the recovery fluid. It has been found that generally a recovery fluid comprising as an ammonium salt, ammonium chloride, is highly effective.

The removal of the branched fluorinated emulsifier from the anion exchange resin is typically practiced at room temperature, e.g. at a temperature of 15 to 30° C. However, the method may also be carried out at a higher temperature for example at a temperature between 20 and 80° C. The recovery of the branched fluorinated emulsifier may be somewhat more efficient at such higher temperature although a recovery at higher temperature may increase costs for the recovery. It will generally also be desirable to condition the loaded anion exchange resin by first washing the resin with water followed by a water/organic solvent mixture and optionally finally with the pure organic solvent to remove potential contaminants. Although not necessary for the practice of the method of this disclosure, such conditioning may prevent damaging the anion exchange resin during elution.

As mentioned above, the branched fluorinated emulsifier that is contained in the recovery fluid may be separated therefrom using an appropriate separation method. When the recovered branched fluorinated emulsifier is in a derivatized form, the emulsifier may be further treated to convert and/or purify it back to its original form for subsequent reuse.

In a particular embodiment, when the branched fluorinated emulsifier is one that in its free acid form is steam-volatile, it may be readily separated from the eluate by acidifying the recovery fluid so as to put the branched fluorinated emulsifier in its free acid form and subsequently distilling the recovery fluid to recover the branched fluorinated emulsifier in its free acid form.

In one embodiment, the acid form of the branched fluorinated emulsifier can be purified by standard distillation, preferably under reduced pressure.

If desired, the recovered branched fluorinated emulsifier may be converted into a suitable salt. For example by collecting the distilled branched fluorinated emulsifier in an ammonium solution, the ammonium salt of the branched fluorinated emulsifier may be obtained. It may be desirable to remove the organic solvent(s) used from eluate prior to converting the branched fluorinated emulsifier in its free acid form. Thus, the organic solvent and water may first be removed by distillation and subsequently the remaining mixture may be acidified to convert the branched fluorinated emulsifier in its free acid form followed by distillation of the branched fluorinated emulsifier.

U.S. Pat. Publ. No. 2009/281261 (Brothers, et al.), which is directed toward abatement of fluoroether containing carboxylic acids or salts thereof in fluoropolymer manufacture recognizes that the branched fluoroether carboxylic acids and salts thereof decarboxylate at lower temperatures. Although not wanting to be limited by theory, it is believed that the branched fluorinated emulsifier comprising the at least one ether linkage, not only are more susceptible to decarboxylation, but are also more water soluble than its linear counterparts. Therefore, the distillation process is not as effective with the branched fluorinated emulsifiers and consequently reduced pressures are applied to avoid decarboxylation.

In one embodiment, the branched fluorinated emulsifier can be purified to the acid form using the oxidation process as described in U.S. Pat. No. 5,312,935 (Mayer et al.) This patent describes treating an emulsifier, e.g., a sodium salt of perfluorooctanoic acid in an aqueous acid solution with an oxidizing agent (e.g. APS) at higher temperatures (60° C. to the boiling point of the mixture).

In the present disclosure, not only is the branched fluorinated emulsifier removed from the waste stream or dispersion, the branched fluorinated emulsifier that is recovered, can optionally be regenerated, and/or purified for re-use. The recovered branched fluorinated emulsifier can be used in an aqueous emulsion polymerization of one or more fluorinated monomers according to the procedures known for aqueous emulsion polymerization of fluorinated monomers. Examples of fluorinated monomers that may be emulsion polymerized using the recovered branched fluorinated emulsifier include gaseous fluorinated monomers including partially and fully fluorinated gaseous monomers such as fluorinated olefins including tetrafluoroethylene, hexafluoropropylene, vinylidene fluoride, vinyl fluoride, fluorinated vinyl ethers and in particular perfluorinated vinyl ethers such as perfluoromethylvinyl ether. The fluorinated monomers may be copolymerized with further monomers, which may not be fluorinated such as for example olefins such as ethylene and propylene.

Exemplary embodiments of the present disclosure are described below:

Embodiment 1

A process for recovering a fluorinated emulsifier from an anion exchange resin, comprising
contacting the anion exchange resin with a recovery fluid to form an eluate, the recovery fluid comprising an ammonium salt, water, and a water-miscible solvent, wherein the fluorinated emulsifier is of the formula:

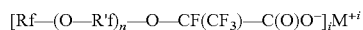

wherein Rf is a fluorinated alkyl group comprising 1 to 5 carbon atoms; R'f is a divalent fluorinated group comprising 1 to 5 carbon atoms; n is 0, 1, 2, or 3; and $M^{+i}$ represents a cation having the valance i and i is 1, 2 or 3; and separating the anion exchange resin from the eluate.

Embodiment 2

The process of embodiment 1, wherein the fluorinated emulsifier is selected from at least one of: (i) n=0 and Rf=$CF_3(CF_2)_2$—; and (ii) n=1 and Rf=$CF_3$— and R'f=—$CF(CF_3)CF_2$—.

Embodiment 3

The process of any one of embodiments 1-2, wherein the ammonium salt is of the formula:

wherein each R is independently selected from H and an alkyl group comprising 1-5 carbon atoms; n is 1 or 2; and X is selected from F, Cl, Br, I, and an anionic organic residue.

Embodiment 4

The process of any one of embodiments 1-3, wherein the water-miscible solvent is an aliphatic alcohol having between 1-5 carbon atoms.

Embodiment 5

The process of any one of embodiments 1-4, wherein the recovery fluid is substantially free of a strong acid.

Embodiment 6

The process of any one of embodiments 1-5, wherein the recovery fluid has a pH greater than 6.

Embodiment 7

The process of any one of embodiments 1-6, wherein an amount of the ammonium salt is 0.2 to 5 wt % as compared to the total weight of the recovery fluid.

Embodiment 8

The process of any one of embodiments 1-7, wherein the contacting is conducted at a temperature of 20 to 80° C.

Embodiment 9

The process of any one of embodiments 1-8, wherein the % wt of the water-miscible solvent to the total weight of the recovery fluid is 50 wt % to 99 wt %.

Embodiment 10

The process of any one of embodiments 1-9, further comprising: removing the water and water-miscible solvent from the eluate to provide a concentrate.

Embodiment 11

The process of any one of the previous embodiments, further comprising acidifying the eluate or the concentrate to generate the free acid form of the fluorinated emulsifier.

Embodiment 12

The process of any one of the previous embodiment, further comprising distilling eluate, concentrate, and/or the free acid form of the fluorinated emulsifier.

Embodiment 13

The process of any one of the previous embodiment, further comprising regenerating the fluorinated emulsifier back to its original form.

EXAMPLES

Advantages and embodiments of this disclosure are further illustrated by the following examples, but the particular materials and amounts thereof recited in these examples, as well as other conditions and details, should not be construed to unduly limit this invention. In these examples, all percentages, proportions and ratios are by weight unless otherwise indicated.

All materials are commercially available, for example from Sigma-Aldrich Chemical Company; Milwaukee, Wis., or known to those skilled in the art unless otherwise stated or apparent.

These abbreviations are used in the following examples: g=gram, kg=kilograms, min=minutes, mol=mole;

cm=centimeter, hr=hour; mm=millimeter, ml=milliliter; L=liter; mbar=millibar; and wt=weight.

Materials

Anion exchange resin: strong basic ion exchange resin comprising quaternary amine functional group ($N^+(CH_3)_4$), available under the trade designation "AMBERJET 4200 OH" available from Dow Chemical Co., Midland, Mich.

Emulsifier 1: $CF_3$—$CF_2$—$CF_2$—O—$CF(CF_3)$—C(O)—$O^-K^+$ available from Anles, St. Petersburg, Russia.

Emulsifier 2: $CF_3$—O—$CF_2$—$CF_2$—$CF_2$—O—CHF—$CF_2$—C(O)— $O^-NH_4^+$ which can be synthesized as described in Preparation of compound 11 as described in U.S. Pat. Publ. No. 2007/0025902.

Comparative Example 1

A recovery fluid was prepared comprising 60 wt % methanol, 20 wt % water, and 20 wt % sulfuric acid (concentrated).

300 ml of Anion exchange resin was mixed with an aqueous solution containing 55 g of Emulsifier 2 in a 1-L flask, for 24 hr on a roller. The loaded resin then was transferred into a column (forming an ion exchange column) and washed with 3 L of deionized water.

600 mL of the recovery fluid (above) was circulated for 5 hours through the column with a flow of about 1.5 L/hr. The recovery fluid was pumped from the top of a feeding tank through the column and back into the feeding tank (flow direction through the column from top to bottom). The elution was done at room temperature. During the recovery step, phase separation occurred in the tank due to the formation of the corresponding methylester ($CF_3$—O—$CF_2$—$CF_2$—$CF_2$—O—CHF—$CF_2$—C(O)— O—$CH_3$). The lower phase, essentially consisting of the corresponding methylester, was separated.

The resin was washed with 1.8 L of a methanol/water (90:10 wt-%) solution followed by 1.2 L of deionized water. Both washes were with a flow rate of 300 ml/hr. The washing solutions and the upper phase of the tank were allowed to stand for a period of 16 hours to achieve additional phase separation. The lower phase was separated and added to the methylester phase from above. The remaining upper phase in the tank, mainly comprising methanol, water, sulphuric acid and residual methylester derivative of the emulsifier, was rectified (distilled) under atmospheric pressure. The purified methanol contained a small amount (<10 ppm) of the methylester derivative of Emulsifier 2 and was used for a subsequent regeneration process. The regenerated anion exchange resin also could be re-used.

The total amount of the methyl ester derivative of Emulsifier 2 collected was determined by GC (gas chromatography) using a calibration curve made with the corresponding methylester of the emulsifier. The overall recovery efficiency of the emulsifier was calculated to be about 85.4%.

Comparative Example 2

A recovery fluid was prepared comprising 60 wt % methanol, 20 wt % water, and 20 wt % sulfuric acid (concentrated).

300 ml of Anion exchange resin loaded with 46.8 g of Emulsifier 2 (degree of loading=0.16 g per ml of resin) was transferred to a distillation apparatus consisting of a flask equipped with a mechanical stirrer, a thermometer, a condenser, a separator and a heating jacket.

The recovery fluid (600 ml) was added to the flask. The mixture was refluxed and the condensed vapors separating in two liquid phases. The lower phase was removed while the upper phase was sent back to the distillation flask. More than 90% of the lower phase was separated in the first 5 hours of the distillation. The distillation was finished when no increase of the lower phase was observed (approximate distillation time of 8 hr). The total lower phase of the distillate (43.8 g) consisted of the methylester derivative (degree of purity=96%). The lower phase was analyzed by GC using a calibration curve made with the corresponding methylester of the emulsifier.

The anion exchange resin was separated (e.g., by filtration or decantation) from the remaining liquid (upper phase) in the flask. The liquid consisted of methanol, water, sulfuric acid, and residual methylester derivative. This liquid was distillated under atmospheric pressure. The purified methanol contained a very small amount of the methylester derivative of Emulsifier 2 and was used for a subsequent regeneration process. The regenerated ion-exchange resin also could be re-used.

The lower phase (43.8 g), consisting of the methylester derivative ($CF_3$—O—$CF_2$—$CF_2$—$CF_2$—O—CHF—$CF_2$—C(O)— O—$CH_3$, 96%) was purified in a further step via fractionated distillation. 41.5 g (recovery rate=90%) of the methylester derivative was collected at a boiling point of about 60° C. at 30 mbar. The methylester derivative was saponified with aqueous ammonia solution (100% conversion) at 60-80° C. to yield Emulsifier 2 and the methanol was removed by distillation.

The resulting aqueous solution of Emulsifier 2 ($CF_3$—O—$CF_2$—$CF_2$—$CF_2$—O—CHF—$CF_2$—C(O)— $O^-NH_4^+$) was used as an emulsifier for tetrafluorethylene polymerization to show "polymerization grade" of the product after the recycling process. No deviation between virgin and recycled emulsifier was observed during polymerization process.

Comparative Example 3

A recovery fluid was prepared comprising 40 wt % methanol, 40 wt % water, and 20 wt % sulfuric acid (concentrated).

300 ml of a Anion exchange resin loaded with 55 g of Emulsifier 1 (degree of loading=0.18 g per ml of resin) was transferred to a distillation apparatus consisting of a flask equipped with a thermometer, condenser, a separator, a mechanical stirrer and a heating jacket.

The recovery fluid (600 ml) was added to the flask. The mixture was heated under reflux conditions and the condensed vapors separated in two liquid phases.

The lower phase, 36.5 g, consisting of the methylester derivative (degree of purity=89% as measured by GC) was removed while the upper phase was sent back to distillation-flask. The distillation was finished when no increase of the lower phase was observed (approximate distillation time of 24 hr).

The distillation flask, comprising the upper phase, was slowly heated from 83° C. to 100° C., whereby 240 g of methanol was evaporated and condensed into a separate flask over the course of 8 hours. The condensed methanol phase was analyzed by GC using a calibration curve made with the corresponding methylester of the emulsifier and found to contain 1.6 g of methylester derivative.

In total, 36.5 g of the methylester derivative of Emulsifier 1 (degree of purity=89%) from the first distillation and 1.6 g of the methylester derivative of Emulsifier 1 in the condensed methanol phase were found. This corresponded to an overall recovery efficiency of the emulsifier of about 67%.

Comparison Example 4

A recovery fluid was prepared comprising 60 wt % methanol, 20 wt % water, and 20 wt % sulfuric acid (concentrated).

300 ml, which is equal to one bed volume (BV), of Anion exchange resin was mixed with 69.9 g of Emulsifier 1 in a 1-L flask, for 24 hr on a roller for 24 h. The loaded resin then was transferred into a column (forming an ion exchange column) and washed with 1.5 L of deionized water. The degree of loading was 0.2 g of emulsifier per ml of resin.

The recovery fluid (above) was circulated for 5 hours through the column with a flow of 5 BV/hr. The recovery fluid was pumped from the top of a flask through the column and back into the flask (flow direction through the column from top to bottom). During this procedure a lower phase (6.8 g of the methylester derivative of the emulsifier, pure, analyzed by GC) was formed in the flask.

After regeneration, the resin was washed with 1.8 l (=6 BV) of a methanol-water (90:10 wt-%) solution, followed by 1.2 L (=4 BV) of deionized water. Both washes were with a flow rate of 1.5 L/hr, which is equal to 5 BV/hr.

In total, 49.9 g of the methylester derivative of Emulsifier 1 ($CF_3CF_2CF_2$—O—$CF(CF_3)$—C(O)—O—$CH_3$) was found; 6.8 g in the lower phase and 43.1 g recovered from the upper phase and washing solutions (before distillation). The overall recovery efficiency of the emulsifier was calculated to be 76%.

The upper phase and washing solutions from above were distilled to isolate the methylester derivative of the emulsifier. Distillation was performed in a 1-L flask with thermometer, condenser, column, a mechanical stirrer and a heating jacket. The solution was refluxed with reflux ratio of 100:1 for 33 hours. The distillation was finished at a temperature of 118° C. in the distillation residue. The resulting isolated pure methylester (42.3 g) has a boiling point of 109° C. under atmospheric pressure.

Comparative Example 5

152 g of the methylester derivative of Emulsifier 1 ($CF_3$—$CF_2$—$CF_2$—O—$CF(CF_3)$—C(O)—$OCH_3$), 451 g water, and 122 g of a 25% ammonia solution in water were placed in a flask equipped with a thermometer, condenser, a mechanical stirrer, and a thermostate (heater). The mixture was heated at 82° C. for one week. GC analysis of the resulting product indicated that 75% of the $CF_3$—$CF_2$—$CF_2$—O—$CF(CF_3)$—C(O)— $OCH_3$ was converted to $CF_3$—$CF_2$—$CF_2$—O—$CF(CF_3)$—C(O)— $ONH_2$ and 25% was converted to $CF_3$—$CF_2$—$CF_2$—O—$CF(CF_3)$—C(O)—$O^-NH_4^+$.

Example 1

A recovery fluid was prepared comprising 2600 g methanol (87.6 wt %), 300 g water (10 wt %) and 70 g ammonium chloride (2.4 wt %).

300 ml of Anion exchange resin loaded with a solution comprising 55.6 g of Emulsifier 1 (degree of loading=0.18 g per ml resin) was transferred into a column.

The recovery fluid (above) was pumped through column with a flow rate of 2 to 3 BV/hr (1 bed volume corresponds to 300 ml). The recovery fluid was pumped through the column and collected (flow direction through the column from top to bottom). After each bed volume, the amount of the salt derivative ($CF_3$—$CF_2$—$CF_2$—O—$CF(CF_3)$—C(O)—$O^-NH_4^+$) in the eluate was determined by GC. The results are shown in Table 1, below.

TABLE 1

| Bed Volume | Amount of Emulsifier Salt (g) |
| --- | --- |
| 1 | 18.7 |
| 2 | 13.1 |
| 3 | 14.9 |
| 4 | 4.0 |
| 5 | 0.1 |

As shown in Table 1 above, after approximately the first 5 bed volumes of recovery fluid (about 2 hours), nearly the entire amount of the emulsifier is recovered.

The collected eluate (comprising methanol, water, and residual emulsifier) was evaporated (using a rotary evaporator) to remove the methanol and water, leaving the ammonium salt of Emulsifier 1.

After evaporation, 168 ml of sulfuric acid was added to the residue and a phase split occurred. The lower phase comprised perfluorpropoxypropionic acid ($CF_3$—$CF_2$—$CF_2$—O—$CF(CF_3)$—C(O)— OH, 42.4 g, purity: 100%, analyzed by HPLC). The overall recovery efficiency of the emulsifier was calculated to be 87%.

The resin then was washed with 1500 ml (=5 BV) of deionized water using a flow rate of 600 ml/hr (about 2 BV/hr) for reuse.

Foreseeable modifications and alterations of this invention will be apparent to those skilled in the art without departing from the scope and spirit of this invention. This invention should not be restricted to the embodiments that are set forth in this application for illustrative purposes.

What is claimed is:

1. A process for recovering a fluorinated emulsifier from an anion exchange resin, comprising
    contacting the anion exchange resin with a recovery fluid to form an eluate, the recovery fluid comprising an ammonium salt, water, and a water-miscible solvent, wherein the fluorinated emulsifier is of the formula:

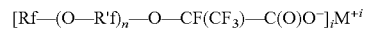
    $[Rf-(O-R'f)_n-O-CF(CF_3)-C(O)O^-]_i M^{+i}$ wherein Rf is a fluorinated alkyl group comprising 1 to 5 carbon atoms; R'f is a divalent fluorinated group comprising 1 to 5 carbon atoms; n is 0, 1, 2, or 3; and $M^{+i}$ represents a cation having the valance i and i is 1, 2 or 3; and
separating the anion exchange resin from the eluate.
2. The process of claim 1, wherein the fluorinated emulsifier is selected from at least one of: (i) n=0 and Rf=$CF_3$ $(CF_2)_2$—; and (ii) n=1 and Rf=$CF_3$— and R'f=—$CF(CF_3)$ $CF_2$—.
3. The process of claim 1, wherein the ammonium salt is of the formula:

    $(NR_4)_n X$ wherein each R is independently selected from H and an alkyl group comprising 1-5 carbon atoms; n is 1 or 2; and X is selected from F, Cl, Br, I, and an anionic organic residue.
4. The process of claim 1, wherein the water-miscible solvent is an aliphatic alcohol having between 1-5 carbon atoms.

5. The process of claim 1, wherein the recovery fluid is substantially free of a strong acid.

6. The process of claim 1, wherein the recovery fluid has a pH greater than 6.

7. The process of claim 1, wherein an amount of the ammonium salt is 0.2 to 5 wt % as compared to the total weight of the recovery fluid.

8. The process of claim 1, wherein the contacting is conducted at a temperature of 20 to 80° C.

9. The process of claim 1, wherein the % wt of the water-miscible solvent to the total weight of the recovery fluid is 50 wt % to 99 wt %.

10. The process of claim 1, further comprising: removing the water and water-miscible solvent from the eluate to provide a concentrate; acidifying the concentrate to generate the free acid form of the fluorinated emulsifier; and distilling the free acid form of the fluorinated emulsifier.

11. The process of claim 1, further comprising distilling eluate, concentrate, and/or the free acid form of the fluorinated emulsifier.

12. The process of claim 1, further comprising regenerating the fluorinated emulsifier back to its original form.

13. The process of claim 1, further comprising removing the water and water-miscible solvent from the eluate to provide a concentrate.

* * * * *